US010646189B2

(12) United States Patent
Jin

(10) Patent No.: US 10,646,189 B2
(45) Date of Patent: May 12, 2020

(54) CONTROLLING MOTION POSITION OF MULTI-LEAF COLLIMATOR

(71) Applicant: Shanghai Neusoft Medical Technology Co., Ltd., Shanghai (CN)

(72) Inventor: Feng Jin, Shenyang (CN)

(73) Assignee: Shanghai Neusoft Medical Technology Co., Ltd., Shanghai (CN)

( * ) Notice: Subject to any disclaimer, the term of this patent is extended or adjusted under 35 U.S.C. 154(b) by 259 days.

(21) Appl. No.: 15/670,286

(22) Filed: Aug. 7, 2017

(65) Prior Publication Data
US 2018/0035969 A1 Feb. 8, 2018

(30) Foreign Application Priority Data
Aug. 8, 2016 (CN) .......................... 2016 1 0647749

(51) Int. Cl.
*A61B 6/00* (2006.01)
*A61N 5/10* (2006.01)
(Continued)

(52) U.S. Cl.
CPC .............. *A61B 6/542* (2013.01); *A61B 6/06* (2013.01); *A61N 5/1077* (2013.01); *G21K 1/046* (2013.01); *A61N 5/1045* (2013.01); *G08C 23/06* (2013.01)

(58) Field of Classification Search
CPC .............. A61B 6/54; A61B 6/542; A61B 6/06
(Continued)

(56) References Cited

U.S. PATENT DOCUMENTS 8,610,077 B2 * 12/2013 Beaulieu ................. G01T 1/201
250/252.1
2003/0183788 A1 * 10/2003 Pastyr .................... G01B 7/003
250/505.1
(Continued)

FOREIGN PATENT DOCUMENTS

CN 101739034 A 6/2010
CN 102117051 A 7/2011
(Continued)

OTHER PUBLICATIONS

English DERWENT Abstract for CN-205843700-U (Year: 2016).*
(Continued)

*Primary Examiner* — David P Porta
*Assistant Examiner* — Abra S Fein
(74) *Attorney, Agent, or Firm* — Fish & Richardson P.C.

(57) ABSTRACT

Methods and devices for controlling a motion position of a multi-leaf collimator are provided. An example device includes a control system and two trolleys connected with the control system. The multi-leaf collimator includes two rows of leaves arranged in opposite sides, and each of the trolleys carries one row of the leaves. Each trolley is movably connected with a first screw rod and driven by a first motor connected with the first screw rod. A first encoder is arranged on the first motor and operable to feed back first position information of the trolley to the control system. A displacement sensor is arranged on the first screw rod and operable to feed back second position information of the trolley to the control system. The control system is operable to control the motion position of the trolley based on the first position information and the second position information.

18 Claims, 5 Drawing Sheets

(51) Int. Cl.
*A61B 6/06* (2006.01)
*G21K 1/04* (2006.01)
*G08C 23/06* (2006.01)

(58) Field of Classification Search
USPC .......................................... 378/151; 382/291
See application file for complete search history.

(56) References Cited

U.S. PATENT DOCUMENTS

| | | | | |
|---|---|---|---|---|
| 2006/0072849 | A1* | 4/2006 | Marc .................... | A61N 5/1042 |
| | | | | 382/291 |
| 2006/0256915 | A1 | 11/2006 | Otto et al. | |
| 2008/0073591 | A1* | 3/2008 | Mohr .................... | A61N 5/1042 |
| | | | | 250/494.1 |
| 2010/0106100 | A1* | 4/2010 | Petersen ................ | A61M 5/24 |
| | | | | 604/232 |
| 2012/0043481 | A1* | 2/2012 | Mansfield ............. | G21K 1/046 |
| | | | | 250/492.1 |
| 2012/0085909 | A1* | 4/2012 | Chen .................... | G01K 11/006 |
| | | | | 250/338.1 |

FOREIGN PATENT DOCUMENTS

| | | | |
|---|---|---|---|
| CN | 102915784 | A | 2/2013 |
| CN | 104147712 | A | 11/2014 |
| CN | 105425646 | A | 3/2016 |
| CN | 205843700 | U * | 12/2016 |
| JP | 2007319497 | A | 12/2007 |
| JP | 2010005149 | A | 1/2010 |
| RU | 2591233 | C1 * | 7/2016 |
| WO | 2005018742 | A1 | 3/2005 |
| WO | 2012171538 | A1 | 12/2012 |

OTHER PUBLICATIONS

English DERWENT Abstract for RU-2591233-C1 (Year: 2016).*
European Patent Office: European Search Report mailed in corresponding European Patent Application No. 17179966.1 dated Nov. 24, 2017 (7 pages).
State Intellectual Property Office of the People's Republic of China, Office Action and Search Report Issued in Application No. 201610647749.4, dated Oct. 31, 2018, 11 pages, (Submitted with English- language machine translation).
State Intellectual Property Office of the People's Republic of China, Office Action and Search Report Issued in Application No. 201610647749.4, dated May 13, 2019, 15 pages. (Submitted with Machine Translation).

* cited by examiner

US 10,646,189 B2

CONTROLLING MOTION POSITION OF MULTI-LEAF COLLIMATOR

CROSS REFERENCE TO RELATED APPLICATIONS

The present disclosure claims priority to Chinese Patent Application No. 201610647749.4 filed on Aug. 8, 2016, the entire content of which is incorporated herein by reference.

TECHNICAL FIELD

The present disclosure relates to controlling a motion position of a multi-leaf collimator in a medical electronic linear accelerator.

BACKGROUND

With rapid development of radiotherapy technology, conformal radiotherapy and intensity modulated radiotherapy have become main technologies for daily use in hospitals. A problem for radiotherapy is how to minimize a radiation dose suffered by a healthy tissue of a patient, at least to maintain the radiation dose lower than a detrimental threshold, and simultaneously how to expose a cancer tissue to a significantly detrimental radiation dose.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

SUMMARY

The present disclosure provides methods and devices for controlling a motion position of a multi-leaf collimator in a medical electronic linear accelerator, which can achieve double-detection check on a motion position of each leaf on the multi-leaf collimator to form a desired irradiation field for a lesion site of a patient and avoid overshoot of the leaf, thereby improving safety of patients and operators and increasing reliability of the medical electronic linear accelerator.

One aspect of the present disclosure features a device for controlling a motion position of a multi-leaf collimator, the multi-leaf collimator having two rows of leaves arranged in opposite sides. The device includes a control system, two trolleys connected with the control system, each of the trolleys carrying a respective row of the leaves and is movably connected with a first screw rod and driven by a first motor connected with the first screw rod, a first encoder arranged on the first motor and operable to feed back first position information of the trolley to the control system, and a displacement sensor arranged on the first screw rod and operable to feed back second position information of the trolley to the control system. The control system is operable to control the motion position of the trolley based on the first position information and the second position information.

In some cases, the device further includes a limit switch arranged on at least one end of the first screw rod, and the limit switch is in communication with the control system. In some cases, the device further includes a first approaching switch arranged between a center of the first screw rod and the limit switch in a way that the first approaching switch has a preset distance with the limit switch, and the first approaching switch is in communication with the control system.

In some implementations, the device further includes a first position detecting switch and a second position detecting switch arranged between the limit switch and the first approaching switch on the first screw rod. The first position detecting switch and the second position detecting switch are in communication with the control system. The first position detecting switch is connected in series with a first relay in communication with the control system. The second position detecting switch is connected in series with a second relay connected in parallel with the first relay, and the second relay is connected in parallel with the first motor to electrically control a power supply of the first motor. In some cases, the first position detecting switch is set as a normally open contact, the second position detecting switch is set as a normally closed contact, the second position detecting switch is connected in parallel with a normally open contact of the first relay, and the first motor is connected in parallel to a normally open contact of the second relay.

In some implementations, each row of the leaves includes a plurality of leaves, and each of the leaves is driven by a respective second screw rod and a respective second motor. A second encoder can be arranged on the second motor and operable to feed back fourth position information of the leaf to the control system. A thin film potentiometer can be arranged on the leaf and operable to feed back fifth position information of the leaf to the control system. The control system can be operable to control a motion position of the leaf based on the fourth position information and the fifth position information.

The device can further include an optical fiber sensor arranged on an end side of each row of the leaves. The optical fiber sensor can include a light emitting head and a light receiving head. The light emitting head and the light receiving head are respectively arranged at two opposite ends of the end side, and the light receiving head is in communication with the control system.

The device can further include a photoelectric sensor arranged on a center line between the two rows of leaves and on an outside of the two rows of leaves. The photoelectric sensor can be in communication with the control system.

The device can further include a second approaching switch arranged on two sides of a center line between the two rows of leaves and on an outside of the two rows of leaves. The second approaching switch can be in communication with the control system.

The device can further include at least one guide rail parallel to the first screw rod. Each of the trolleys can be movably connected with the at least one guide rail.

Another aspect of the present disclosure features a linear accelerator including: a multi-leaf collimator having two rows of leaves arranged on opposite sides; and a motion position controlling device. The motion position controlling device includes: a control system; two trolleys connected with the control system, each of the trolleys carrying a respective row of the leaves and is movably connected with a first screw rod and driven by a first motor connected with the first screw rod; a first encoder arranged on the first motor and operable to feed back first position information of the trolley to the control system; and a displacement sensor arranged on the first screw rod and operable to feed back second position information of the trolley to the control system. The control system is operable to control the motion position of the trolley based on the first position information and the second position information.

In some implementations, each row of the leaves includes a plurality of leaves, and each of the leaves is driven by a respective second screw rod and a respective second motor. A second encoder is arranged on the second motor and operable to feed back fourth position information of the leaf to the control system. A thin film potentiometer is arranged on the leaf and operable to feed back fifth position information of the leaf to the control system, and the control system is operable to control a motion position of the leaf based on the fourth position information and the fifth position information.

A further aspect of the present disclosure features a method of controlling a motion position of a multi-leaf collimator. The method includes: transmitting a control signal to a first motor to drive a trolley to move, the trolley being movably connected to a first screw rod and carrying a row of leaves arranged on a side of the multi-leaf collimator; receiving first position information of the trolley from a first encoder arranged on the first motor; receiving second position information of the trolley from a displacement sensor arranged on the first screw rod; comparing the first position information with the second position information to determine whether the first position information is coincident with the second position information; and when the first position information is determined not to be coincident with the second position information, adjusting a rotation angle of the first motor to correct a deviation of the motion positon of the trolley.

The method can further include: receiving third position information of the trolley from a limit switch when the trolley is at an origin position, wherein the limit switch is located on an end of the first screw rod; comparing the third position information with the first position information and the second position information, respectively; when the first position information is determined not to be coincident with the third position information based on a result of the comparison, performing a reset calibration for Z axis of the first motor; when the second position information is determined to be neither coincident with the first position information nor the third position information based on the result of the comparison, calibrating at least one of the Z axis of the first motor or a position of the limit switch; and when any two of the first position information, the second position information, and the third position information are determined not to be coincident with each other based on the result of the comparison, cutting off a power supply to the multi-leaf collimator.

The method can further include: receiving motion position information of the trolley detected by a first approaching switch when the trolley moves along the first screw rod to the first approaching switch, wherein the first approaching switch is located between the limit switch and a center of the first screw rod and has a preset distance with the limit switch, and controlling the first motor to decelerate rotation based on the received motion position information in a way that the trolley is capable of stopping at the limit switch.

In some implementations, the method further includes: transmitting a second control signal to a second motor to drive one of leaves to move, each of the leaves being movably connected to a respective second screw rod and driven by a respective second motor; receiving fourth position information of the leaf from a second encoder arranged on the second motor; receiving fifth position information of the leaf from a thin film potentiometer arranged on the leaf; comparing the fourth position information with the fifth position information to determine whether the fourth position information is coincident with the fifth position information; and when the fourth position information is determined not to be coincident with the fifth position information, adjusting a rotation angle of the second motor to correct a position deviation of the leaf.

In some cases, the method further includes: receiving sixth position information of the leaf from an optical fiber sensor when the leaf is at an origin position, wherein the optical fiber sensor is located on an end side of the row of leaves to which the leaf belongs; comparing the sixth position information with the fourth position information and the fifth position information, respectively; when the sixth position information is determined not to be coincident with the fourth position information based on a result of the comparison, performing a reset calibration for Z axis of the second motor; when the fifth position information is determined to be neither coincident with the fourth position information nor the sixth position information based on the result of the comparison, calibrating at least one of the Z axis of the second motor or the position of the optical fiber sensor; and when any two of the fourth position information, the fifth position information, and the sixth position information are determined not to be coincident with each other based on the result of the comparison, cutting off a power supply to the multi-leaf collimator.

In some cases, the method further includes: receiving a position information of the leaf from a photoelectric sensor, wherein the row of leaves is opposite to a second row of leaves carried by a second trolley and arranged on a second, opposite side of the multi-leaf collimator, and wherein the photoelectric sensor is arranged on a center line between the two rows of leaves and on an outside of the two rows of leaves; and performing a hysteresis compensation for the second screw rod according to the position information received from the photoelectric sensor.

In some cases, the method further includes: receiving a position information of the leaf from a second approaching switch when the leaf moves along the second screw rod to a maximum stroke position, wherein the row of leaves is opposite to a second row of leaves carried by a second trolley and arranged on a second, opposite side of the multi-leaf collimator, and wherein the second approaching switch is arranged at one of two sides of a center line between the two rows of the leaves and on an outside of the two rows of leaves; and controlling the second motor to stop rotating according to the position information received from the second approaching switch.

Other embodiments of this aspect include corresponding computer systems, apparatus, and computer programs recorded on one or more computer storage devices, each configured to perform actions of the method described above. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

The details of one or more examples of the subject matter described in the present disclosure are set forth in the accompanying drawings and description below. Other features, aspects, and advantages of the subject matter will become apparent from the description, the drawings, and the claims. Features of the present disclosure are illustrated by way of example and not limited in the following figures, in which like numerals indicate like elements.

DETAILED DESCRIPTION

Figure 1:
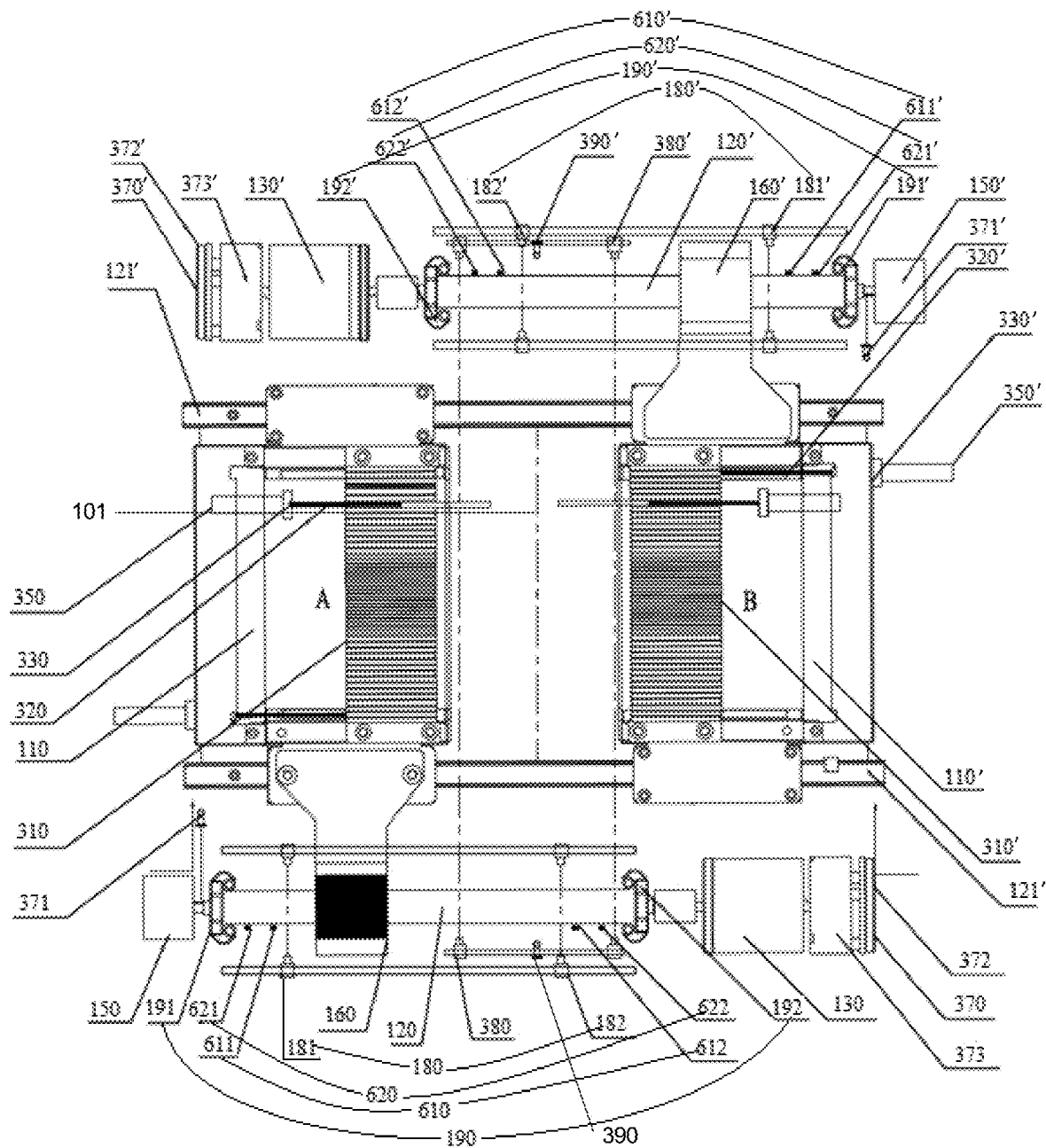
FIG. 1 is a schematic diagram illustrating a structure of a multi-leaf collimator according to one or more examples of the present disclosure.

A medical electronic linear accelerator can be used for implementing a set-up control to perform conformal radiotherapy and/or intensity modulated radiotherapy. For example, a medical electronic linear accelerator with a Multi-Leaf Collimator (MLC) can be used for tumour treatment. The MLC can form various view shapes of fields suitable for patients during motion processes, which can improve a radiotherapy gain ratio. In particular, a radioactive ray dose can be as concentrated as possible to a lesion of a patient to kill tumours or cancer cells, so that surrounding normal tissues and organs can suffer less unwanted radiation, or cannot suffer unwanted radiation.

An MLC device includes groups A and B of a plurality of pairs of high-density tungsten alloy leaves arranged in opposite directions on the left and right sides, so as to shield X-rays. Each leaf may be driven by its respective motor to achieve independent motion. A required irradiation field shape may be quickly formed by detecting and controlling opposite motions of leaves through a control system. As the leaves can shield rays, the rays may pass through only the irradiation field that is not covered by the leaves. In combination with a rotation motion of a gantry of a medical electronic linear accelerator, modulated radiotherapy may be accurately achieved.

The MLC device can effectively control a position and a size of the field formed by opening leaves and closing leaves according to a condition of a size and a position of an actual lesion of a patient, so as to achieve a targeted treatment for the lesion of the patient. Thus, the precise control of motion positions of the leaves in the MLC device can ensure that a lesion site of a patient receives a required X-ray dose, and a healthy tissue of a patient is avoided to be exposed in X-ray irradiation, thereby ensuring safety of patients, hospital operators and the device.

In some implementations, according to an MLC control structure of the medical electronic linear accelerator, displacement feedback information may be exchanged by driving X axis and Y axis of an encoder of a motor associated with each leaf, a value of each encoder may be collected by a host computer software, and an actual motion position of the leaf may be determined and obtained. Alternatively, the position of the leaf drove by the motor may be tracked by the host computer software algorithm. When a designated position may not be reached, calculation compensation may be performed, so that an exact motion position of the current leaf may be determined. Since the calculation may be performed according to the number of fixed pulses sent out when the encoder rotates a circle, a number of the encoder read when the encoder is in a start position, a number of the encoder read when the encoder is in a stop position, when overshoot of the motor occurs or the original position of the device is not accurate, the position information of the current leaf may not be accurately obtained.

The present disclosure provides methods and devices for controlling a motion position of a multi-leaf collimator in a medical electronic linear accelerator by implementing double-detection check for a motion position of a trolley, double-detection check for a motion position of each leaf, and avoiding overshoots of the trolley and the leaves, which can effectively form an irradiation field with a suitable shape and size, such that a healthy site of a patient can be avoided to be suffered from unnecessary X-ray irradiation, safety of patients and medical workers can be protected, and reliability of the medical linear accelerator can be improved.

An exemplary embodiment will be described in detail herein, examples of which are shown in the accompanying drawings. When the following description refers to the accompanying drawings, the same numerals in the different drawings denote the same or similar elements unless otherwise indicated. The implementations described in the following exemplary embodiment are not representative of all implementations coincident with the present disclosure. In contrast, they are merely examples of devices and methods coincident with some aspects of the present disclosure as detailed in the appended claims.

Figure 2:
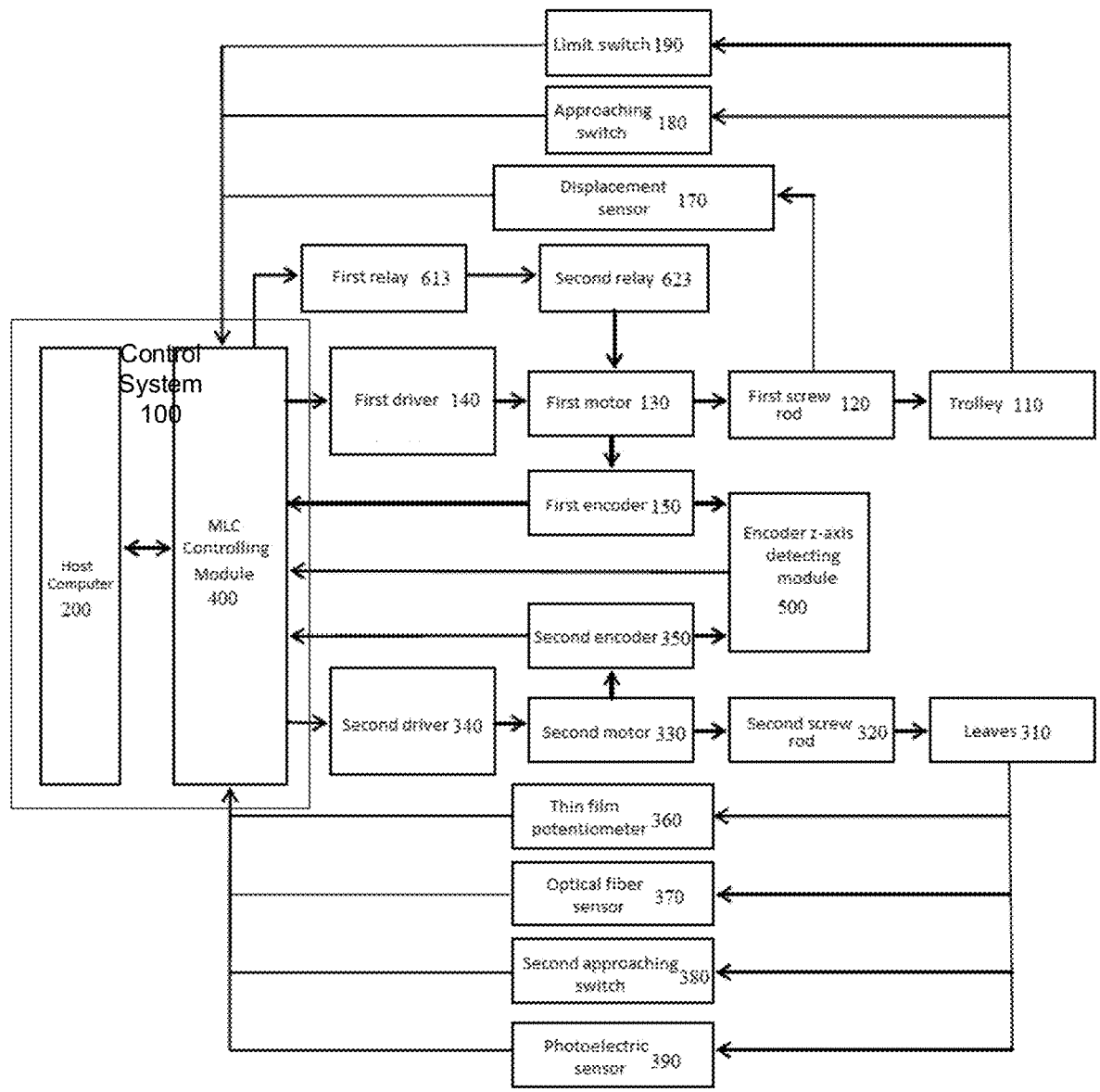
FIG. 2 is a schematic diagram illustrating a functional structure of a device of controlling a motion position of a multi-leaf collimator according to one or more examples of the present disclosure.

Referring to FIGS. 1 to 2, in an example, a device of controlling a motion position of a multi-leaf collimator is illustrated. The device includes a control system 100, a trolley 110, a first screw rod 120, a first motor 130 with a first encoder 150, and a displacement sensor 170 (shown in FIG. 2). The trolley 110 is connected with the control system 100, and may be movably connected with the first screw rod 120. An end of the first screw rod 120 is connected with the first motor 130, and the displacement sensor 170 is provided on the first screw rod 120, which is used for detecting a movement distance of the trolley 110 on the first screw rod 120 in real time. The control system 100 can transmit (or send) one or more control signals to control the motion of the trolley 110 and the leaves 310. Meanwhile, the control system receives actual motion parameters fed back from the trolley 110 and the leaves 310, and performs analysis processing. For example, the displacement sensor 170 and the first encoder 150 can communicate (e.g., by being electrically connected) with the control system 100 to feed respective position information of the trolley 110 back to the control system 100 in real time. The control system 100 can compare the respective position information from the displacement sensor 170 and the first encoder 150 to determine whether they are coincident and transmit control signals to control the motions of the displacement sensor 170 and the first encoder 150 based on a result of the determination. Thus, the double-detection check can be implemented for the motion position of the trolley 110, so that the motion position of the trolley 110 can initially and precisely control motion positions of leaves 310.

A plurality of leaves 310 is positioned on the trolley 100. Each leaf can be provided with a thin film potentiometer 360 and a second motor 330 with a second encoder 350. The thin film potentiometer 360 and the second encoder 350 are in communication (e.g., electrically connected) with the control system 100. A motion positon of each leaf 310 can be independently controlled. For example, the control system 100 can transmit control signals to a second motor 330 for the leaf 310, and the leaf 310 is independently driven by a second screw rod 320 and the second motor 330, so as to precisely control the motion position of the leaf 310. As discussed later, the motion position of each leaf 310 can be detected in real time by the thin film potentiometer 360 and the second encoder 350, respectively, so as to implement double-detection check for the motion position of each leaf. Thus, an irradiation field can be formed, whose shape and size are similar to that of a lesion site of a patient, thereby improving safety of the device.

In an example, a center line 101 between trolley 110 (as illustrated as A in FIG. 1) and trolley 110' (as illustrated as B in FIG. 1) may be taken as an isocenter line. The trolley 110 and the trolley 110' can be symmetrically arranged on left and right sides of the isocenter line.

The leaves 310, 310' on the two trolleys 110, 110' are arranged in opposite sides on two rows, and an end of each row of the leaves 310, 310' is provided with an optical fiber sensor 370. The optical fiber sensor 370 includes a light emitting head 371 and a light receiving head 372, where the light emitting head 371 and the light receiving head 372 are respectively provided on two ends of a same side of each row of the leaves 310, 310'. The light receiving head 372 is electrically connected with the control system 100. Thus, an origin motion position of each row of leaves 310, 310' may be detected and calibrated.

In addition, at least one photoelectric sensor 390 is provided on the center line 101 between the two rows of the leaves 310, 310' and on the outside of the two rows of leaves 310, 310'. The photoelectric sensor 390 may be in communication (e.g., electrically connected) with the control system 100, so as to compensate motion hysteresis of the second screw rod 320 due to abrasion itself, where the second screw rod 320 drives the leaves 310 to move. The photoelectric sensor 390 can be also configured to avoid that overshoot of the leaves 310 occurs due to a fast movement velocity after the leaves 310 move through the center line 101, which may cause that the leaves 310 collides with the opposite leaves.

Further, at least one second approaching switch 380 and at least one second approaching switch 380' are provided on two sides of the center line 101 of the two rows of the leaves 310, 310' and on the outside of the two rows of the leaves 310, 310'. Each second approaching switch 380, 380' may be in communication (e.g., electrically connected) with the control system 100 to determine a stroke range of the leaves 310, so as to avoid that the leaves 310 move beyond the maximum stroke range, and collide with the opposite leaves.

To limit the motion range of the trolley 110, a limit switch 190 is provided on at least one end of the first screw rod 120 to detect and check the origin position of the trolley 110. Each limit switch 190 may be in communication (e.g., electrically connected) with the control system 100.

To avoid that overshoot of the trolley 110 occurs due to the motion of the trolley 110, at least one first approaching switch 180 is provided on a position between the limit switch 190 and a center of the first screw rod 120 in a way that the first approaching switch 180 is has a preset distance with the limit switch 190. For example, the first approaching switch 180 is oriented toward the center of the first screw rod 120. The first approaching switch 180 may be in communication with (e.g., electrically connected to) the control system 100.

A first position detecting switch 610 and a second position detecting switch 620 are provided between the limit switch 190 on the first screw rod 120 and the corresponding first approaching switch 180. The first position detecting switch 610 is connected in series with a first relay 613. The second position detecting switch 620 is connected in series with a second relay 623, and is connected in parallel with the first relay 613. The second relay 623 is connected in parallel with the first motor 130 to electrically control a power supply of a motor on and off, so as to further avoid that overshoot for the trolley 110 occurs due to the motion of the trolley 110.

According to an example of the present disclosure, the first position detecting switch 610 and the second position detecting switch 620 are set as a normally open contact and a normally closed contact, respectively. The second position detecting switch 620 and the first motor 130 are respectively connected in parallel with a normally open contact of the first relay 613 and a normally open contact of second relay 623. The first position detecting switch 610, the second position detecting switch 620, and the first relay 613 may be in communication (e.g., electrically connected) with the control system 100.

In the example, at least one guide rail 121 parallel to the first screw rod 120 may be included. The trolley 110 is movably connected with the guide rail 121.

In an example, as shown in FIG. 2, the control system 100 includes a host computer 200 and a MLC controlling module 400. As shown in FIG. 1, trolleys may include a trolley 110 and a trolley 110'. The trolley 110 and the trolley 110' are symmetrically arranged on left and right sides. The trolley 110' is provided with a plurality of leaves 310, and the trolley 110' is provided with a plurality of leaves 310', where the leaves 310 and the leaves 310' respectively include a plurality of independent leaves, and the number of the leaves 310 is same as that of the leaves 310'. For example, the leaves 310 include 51 independent leaves, and the leaves 310' also include 51 independent leaves. The leaves 310 and the leaves 310' are arranged into two rows in opposite sides.

A lower end of the trolley 110 is connected with a slider 160. Another end of the slider 160 is movably connected with the first screw rod 120. An end of the first screw rod 120 is connected with a first motor 130' via a coupling element. The first motor 130 drives the first screw rod 120 to perform rotation, further to drive the slider 160 to move linearly forward or backward along with the first screw rod 120. In an example of the present disclosure, motion toward the isocenter line 101 between the two trolleys 110, 110' is referred to as forward motion, and motion far away from the isocenter line 101 between the two trolleys 110, 110' is referred to as backward motion.

Similarly, a slider 160' is connected with an upper end of the trolley 110'. Anther end of the slider 160' is movably connected with a first screw rod 120'. An end of the first screw rod 120' is connected with a first motor 130' by a coupling element. The first motor 130' drives the first screw rod 120' to perform rotation, further to drive the slider 160' to move linearly forward or backward along with the first screw rod 120'.

Driven by the corresponding first motors 130 and 130', relative motion, opposite motion and following motion may be performed between the trolley 110 and the trolley 110'.

In the example, the slider 160 and the first screw rod 120 are provided below the trolley 110, and the slider 160' and the first screw rod 120' are provided above the trolley 110', which is beautifully designed, and further avoids mutual interference during a moving process.

The MLC controlling module 400 is respectively in communication (e.g., by electrically connected) with the first motor 130 and the first motor 130' through individual first drivers 140 to control the rotations of the first motor 130 and the first motor 130', thereby driving movement of the trolley 110 and the trolley 110'. In addition, the MLC controlling module 400 may further be in communication (e.g., electrically connected) with the host computer 200 to receive an instruction from the host computer 200 in real time and to feed a relevant parameter back to the host computer 200. The host computer 200 can include one or more processors and one or more storage media coupled to the processors. The MLC controlling module 400 can include a control circuit board. In the control system 100, the host computer 200 generates the instruction by analyzing the parameter received from the MLC controlling module 400, and sends the instruction to the MLC controlling module 400. When receiving the instruction, the MLC controlling module 400 analyzes the instruction and converts the instruction to a signal recognizable by one or more corresponding hardware components.

To acquire a moving distance of the trolley 110 and the trolley 110', the first motor 130 is provided with a first encoder 150, and the first motor 130' is provided with a first encoder 150'. Position information detected by the first encoder 150 and the first encoder 150' may be taken as first motion position detecting information of the corresponding trolleys 110, 110'.

A working principle of the first encoder 150 is as follows.

The first encoder 150 may calculate a moving distance of the corresponding slider 160, according to the number of pulses emitted by the first encoder 150 and a length of one pulse, where the calculated moving distance of the trolley 110 is taken as a motion distance of the trolley 110. After determining an origin position (i.e., an initial position) of the trolley 110, the motion position information of the trolley 110 may be determined according to the motion distance and the origin position of the trolley 110.

The working principle of the first encoder 150' is as follows.

The first encoder 150' may calculate a moving distance of the corresponding slider 160' according to the number of pulses emitted by the first encoder 150' and a length of one pulse, and the calculated moving distance is taken as a motion distance of the trolley 110'. After determining the origin position (i.e., the initial position) of the trolley 110', motion position information of the trolley 110' may be determined according to the motion distance and the origin position of the trolley 110'.

Installation positions of the first encoder 150 and the first encoder 150' may be selected according to requirements. For example, the first encoder 150 may be optionally installed on a spindle of the first motor 130 or a shaft end of the first screw rod 120. Similarly, the first encoder 150' may be optionally installed on a spindle of the first motor 130' or a shaft end of the first screw rod 120'.

In an example, the first encoder 150 is connected with a shaft end of the first screw rod 120 to detect the motion position information of the trolley 110. The first encoder 150' is connected with a shaft end of a first screw rod 120' to detect the motion position information of the trolley 110'. The first encoder 150 and the first encoder 150' may be in communication (e.g., electrically connected) with the MLC controlling module 400.

As noted above, a displacement sensor 170 detects the moving distance of the first screw rod 120 as second motion position detecting information of the trolley 110. In an example, the displacement sensor 170 can include a micro linear displacement sensor with a high precision and a small volume. Micro linear displacement sensors may be installed on side surfaces of the first screw rods 120 and 120' to detect the motion position information associated with the corresponding first screw rods 120, 120' in real time. For example, the linear displacement sensors 170 may measure horizontal moving distances of the corresponding sliders 160, 160', and may feed the measured horizontal moving distances back to the host computer 200 through the MLC controlling module 400.

Each leaf 310 may be connected with a second motor 330 through a second screw rod 320. The independent second motor 330 drives a corresponding leaf 310 to linearly move forward or backward. Similarly, each leaf 310' may be connected with a second motor 330' through a second screw rod 320'. The independent second motor 330' drives the corresponding leaf 310' to linearly move forward or backward. Driven by the corresponding second motors 330, 330', relative motion, opposite motion and following motion may be performed between the leaf 310 and the leaf 310'. The second motor 330 or the second motor 330' can include a micro brush motor having a smaller volume and a smaller capacity.

When the second motor 330 drives the corresponding leaf 310 to move, to acquire the motion position of the corresponding leaf 310, a second encoder 350 may be installed on a spindle of the second motor 330 to collect motion position information of the corresponding leaf 310 in real time and to feed the motion position information back to the host computer 200 through the MLC controlling module 400. Similarly, when the second motor 330' drives the corresponding leaf 310' to move, to acquire the motion position of the corresponding leaf 310', a second encoder 350' is installed on the spindle of the second motor 330' to collect motion position information of the corresponding leaf 310' in real time and to feed the motion position information back to the host computer 200 through the MLC controlling module 400.

In an example, the second encoder 350' or the second encoder 350' may include rotary encoders. For example, the second encoder 350 or the second encoder 350' emit 64 pulses per revolution. In operation, the second motor 330 rotates to drive the corresponding leaf 310 to reciprocate. Accordingly, the second encoder 350 directly converts a rotation angle (proportional to displacement of the leaf 310) of the second motor 330 into a pair of pulse sequences CHA and CHB, which have a phase relationship. When the MLC controlling module 400 detects the phase relationship between the CHA and the CHB, a moving direction of the corresponding leaf 310 may be obtained. A motion rate of the corresponding leaf 310 may be calculated according to a period of CHA, and a displacement S of the corresponding leaf 310 may be acquired by performing an integral operation for the CHA, thereby improving anti-interference and reliability of the device and/or the medical electronic linear accelerator. A working principle of the second encoder 350' is similar to that of the second encoder 350, which is not repeatedly described here.

In an example, a thin film potentiometer 360 is installed on a surface of each of leaves 310 and leaves 310'. The film potentiometer 360 may be very small in volume, which is suitable to be installed in a confined space, and is conducive (or configured) to perform precise control for a small and fine position. A resistance value of the thin film potentiometer 360 on the leaf 310 may be changed along with motion of the leaf 310 to generate a voltage value, and the generated voltage value is fed back to the host computer 200 through the MLC controlling module 400. The host computer 200 calculates the motion position information of the corresponding leaf 310 based on the generated voltage value. A resistance value of the thin film potentiometer 360 on the leaf 310' may be changed along with motion of the leaf 310' to generate a voltage value, and the generated voltage value is fed back to the host computer 200 by the MLC controlling module 400. The host computer 200 calculates the motion position information of the corresponding leaf 310' based on the generated voltage value.

In addition, to avoid leaking X-ray from connections of adjacent two leaves, which may cause unnecessary harm to patients or medical workers or the device, the adjacent two leaves are tightly connected on the connections in a concave-convex cooperating manner, so as to avoid leaking the X-ray.

In an example, an encoder-Z-axis detecting module 500 is further included. The encoder-Z-axis detecting module 500 may be in communication (e.g., electrically connected) with the MLC controlling module 400. The encoder-Z-axis detecting module 500 may acquire Z-axis position information of four encoders, such as the first encoder 150, the first encoder 150', the second encoders 350, and the second encoders 350', so as to determine whether the trolleys 110, 110' and the leaves 310, 310' are located at the origin positions.

In an example, a maximum light field irradiation range of the leaves 310 and the leaves 310' is 40 cm*40 cm, where a maximum motion stroke range of the of the trolley 110 or the trolley 110' is 10 cm respectively to the left and right sides of the isocenter line 101. The maximum motion stroke range of each leaf 310 or each leaf 310' is 15 cm respectively to the left and right sides of the isocenter line 101.

In an example, opposite ends of a leaf 310 and a leaf 310' are used as front ends of the leaf 310 and the leaf 310', which may also be referred to as heads, and other ends of the leaf 310 and the leaf 310' opposite to their front ends are used as back ends of the leaf 310 and the leaf 310', which may also be referred to as tails. At respective initial positions (i.e., the trolley 110, the trolley 110', the leaves 310 and the leaves 310' are located at their respective origin positions), the tails of the leaves 310 on the trolley 110 are located at 20 cm to the left side of the isocenter line 101, and the tails of the leaves 310' on the trolley 110' are located at 20 cm to the right side of the isocenter line 101.

When the trolley 110 and the leaves 310 are located in their respective origin positions, the heads and tails of leaves 310 are aligned, respectively. To detect whether the origin position of each leaf 310 on the trolley 110 is accurate, an origin calibration is in demand. An optical fiber sensor 370 may be provided at the left side of the trolley 110. When the trolley 110 and the leaves 310 are located in their respective origin positions, the optical fiber sensor 370 is located on an alignment line of the tails of the leaves 310.

The optical fiber sensor 370 may include a light emitting head 371, an optical fiber (not shown in FIG. 1 and FIG. 2), and a light receiving head 372. An end of the optical fiber is connected with the light emitting head 371, and the other end is connected with the light receiving head 372, so as to send the light emitted from the light emitting head 371 to the light receiving head 372 through the optical fiber.

The light emitting head 371 and the light receiving head 372 are located at ends of a same side of the leaves 310, respectively. The light emitting head 371 and the light receiving head 372 may be in communication (e.g., electrically connected) with the MLC controlling module 400, respectively. In the example, the light emitting head 371 is located at a lower end of the left side of the leaves 310, and the light receiving head 372 is located at an upper end of the left side of the leaves 310. The light emitted from the light emitting head 371 is perpendicular to the motion direction of the leaves 310 (which is the same with the X-ray direction). Specifically, the light emitting head 371 emits a narrow and long infrared ray beam, and the infrared beam is intercepted when the leaves 310 passes through the infrared ray beam.

When the trolley 110' and the leaves 310' are located in their respective origin positions, the heads and tails of leaves 310' are aligned, respectively. To detect whether the origin position of each leaf 310' on the trolley 110' is accurately calibrated, an optical fiber sensor 370' is provided on the right side of the trolley 110'. When the trolley 110' and the leaves 310' are located in their respective origin positions, the optical fiber sensor 370' is located on an alignment line of the tails of the leaves 310'.

The optical fiber sensor 370' includes a light emitting head 371', an optical fiber (not shown in FIG. 1 and FIG. 2), and a light receiving head 372'. An end of the optical fiber is connected with the light emitting head 371', and the other end thereof is connected with the light receiving head 372', so as to send the light emitted from the light emitting head 371' to the light receiving head 372' through the optical fiber.

The light emitting head 371' and the light receiving head 372' are located at ends of a same side of the leaves 310', respectively. The light emitting head 371' and the light receiving head 372' may be in communication (e.g., electrically connected) with the MLC controlling module 400, respectively. In an example, the light emitting head 371' is located at an upper end of the right side of the leaves 310', and the light receiving head 372' is located at a lower end of the right side of the leaves 310'. The light emitted from the light emitting head 371' is perpendicular to the motion direction of the leaves 310' (which is the same as the X-ray direction). The light emitting head 371' emits a narrow and long infrared ray beam, and the infrared ray beam is intercepted when the leaves 310' passes through the infrared ray beam.

Opening and closing of the optical fiber sensor 370 and the optical fiber sensor 370' are respectively controlled by opening and closing of independent relays, respectively. Moreover, the light emitting head 371 and the light emitting head 371' are respectively fixed to an end of the corresponding first screw rod 120 and 120'. In particular, the light receiving head 372 and the light receiving head 372' are respectively fixed to the first motor 130' and the first motor 130 by a clutch 373' and a clutch 373.

The second screw rod 320 drives a leaf 310 to move, and the second screw rod 320' drives a leaf 310' to move. Abrasions of the second screw rod 320 and the second screw rod 320' may be generated due to movement, which further causes that a gap between the leaves 310, 310' are increased, and hysteresis of the backward and forward motions is increased. To address this, at least one photoelectric sensor 390 may be further provided on the isocenter line 101 of the trolley 110 and the trolley 110'. The at least one photoelectric sensor 390 is located on the outside of the leaves 310 and the leaves 310', and may be in communication (e.g., electrically connected) with the MLC controlling module 400.

In an example, there may be two photoelectric sensors 390, which are located on the upper and lower sides of several pairs of leaves 310, 310', respectively, and the two photoelectric sensors 390 may be in communication (e.g., electrically connected) with the MLC controlling module 400.

To prevent the leaves 310, 310' from moving forward beyond the maximum motion stroke range, a second approaching switch 380 and a second approaching switch 380' are provided on the left and right sides of the isocenter line 101, respectively. The second approaching switches 380, 380' are located on the outside of the leaves 310 and 310', respectively. The second approaching switch 380 and the second approaching switch 380' may be in communication (e.g., electrically connected) with the MLC controlling module 400.

In an example, there may be two second approaching switches 380, which may be located on the upper and lower sides of the leaves 310, respectively, and may be at 15 cm to the right side of the isocenter line 101. The two second approaching switches 380 may be in communication (e.g., electrically connected) with the MLC controlling module 400.

There may be two second approaching switch 380' in the present example, which may be located on the upper and lower sides of the leaves 310', respectively, and may be at 15 cm to the left side of the isocenter line 101. The two second approaching switches 380' may be in communication (e.g., electrically connected) with the MLC controlling module 400.

To effectively control the trolley 110 to move within the maximum motion stroke, as noted above, a limit switch 190 can be provided on at least one end of the first screw rod 120, and the limit switch 190 may be in communication (e.g., electrically connected) with the MLC controlling module 400.

In an example, a back-end limit switch 191 and a front-end limit switch 192 are provided at the right and left ends of the first screw rod 120, respectively, which correspond to the origin position and the end position of the motion of the trolley 110, respectively. For example, the back-end limit switch 191 and the front-end limit switch 192 are symmetrically arranged on the left and right sides of a centre position of the first screw rod 120. In the example, the back-end limit switch 191 may be located at 40 cm to the left side of the isocenter line 101, and the front-end limit switch 192 may be located at 10 cm to the right side of the isocenter line 101.

In addition, the back-end limit switch 191 and the front-end limit switch 192 may be in communication (e.g., electrically connected) with the MLC controlling module 400, so as to respectively calibrate the origin position and the end position of the motion of the trolley 110 and to feed a calibration result back to the host computer 200 through the MLC controlling module 400.

When the first motor 130 drives the trolley 110 to move and the trolley 110 moves backward (i.e., to the left) to approach the back-end limit switch 191, or moves forward (i.e., to the right) to approach the front-end limit switch 192, the MLC controlling module 400 may send a stop instruction (or signal) to the first motor 130. However, due to inertia of the motor 130 itself, the trolley 110 may continue to slide for a particular distance, which may cause that the overshoot of the first motor 130A occurs, the trolley 110A exceeds the maximum stroke range, or collides with the back-end limit switch 191A or the front-end limit switch 192A, and the device may even be damaged.

To avoid the overshoot of the trolley 110 occurs due to the motion inertia of the first motor 130, as noted above, a first approaching switch 180 may be provided between the front-end limit switch 191 and the center of the first screw rod 120 in a way that the first approaching switch 180 has a preset distance with the front-end limit switch 191. A first approaching switch 180 may be provided between the front-end limit switch 192 and the center of the first screw rod 120 in a way that the first approaching switch 180 has a preset distance with the front-end limit switch 192. For example, the first approaching switch 180 is oriented toward the center of the first screw rod 120. In some cases, the first approaching switch 180 includes a first back-end approaching switch 181 and a first front-end approaching switch 182. The first back-end approaching switch 181 is located between the back-end limit switch 191 and the center position of the first screw rod 120, and the first front-end approaching switch 182 is located between the front-end limit switch 192 and the center position of the first screw rod 120.

The distance between the back-end limit switch 191 and the first back-end approaching switch 181 is set as a deceleration buffer in which the first motor 130 moves to the left. Similarly, the distance between the front-end limit switch 192 and the first front-end approaching switch 182 is set as a deceleration buffer in which the first motor 130 moves to the right. The deceleration buffer can ensure that the trolley 110 may decelerate when the trolley 110 runs to a safe distance range, for example, when approaching a boundary of a reasonable area range defined by the back-end limit switch 191 and the front-end limit switch 192, so as to prevent the overshoot. The first back-end approaching switch 181 and the first front-end approaching switch 182 may be in communication (e.g., electrically connected) with the MLC controlling module 400.

The first back-end approaching switch 181 is spaced from the back-end limit switch 191 by a preset distance. The first front-end approaching switch 182 is spaced from the front-end limit switch 192 by the same preset distance. The preset distance may be set as 50 mm, or a specific value of the preset distance may also be set according to an actual condition.

In an example, there may be two first back-end approaching switches 181. The two first back-end approaching switches 181 are symmetrically arranged on the upper and lower sides of the first screw rod 120, so as to more timely and accurately perceive that the trolley 110 runs into the deceleration buffer. Similarly, there may also be two first front-end approaching switches 182, and the two first front-end approaching switches 182 are symmetrically arranged on the upper and lower sides of the first screw rod 120.

To further prevent overshoot in the process that the first motor 130 drives the trolley 110 to move to an origin or an end, a first position detecting switch 610 and a second position detecting switch 620 may be further provided on the first screw rod 120. The first position detecting switch 610 may include a first back-end position detecting switch 611 and a first front-end position detecting switch 612. The second position detecting switch 620 may include a second back-end position detecting switch 621 and a second front-end position detecting switch 622. The four position detecting switches may be in communication (e.g., electrically connected) with the MLC controlling module 400.

The first back-end position detecting switch 611 and the second back-end position detecting switch 621 are arranged between the first back-end approaching switch 181 and the back-end limit switch 191. The first front-end position detecting switch 612 and the second front-end position detecting switch 622 are arranged between the first front-end approaching switch 182 and the front-end limit switch 192.

Figure 3:
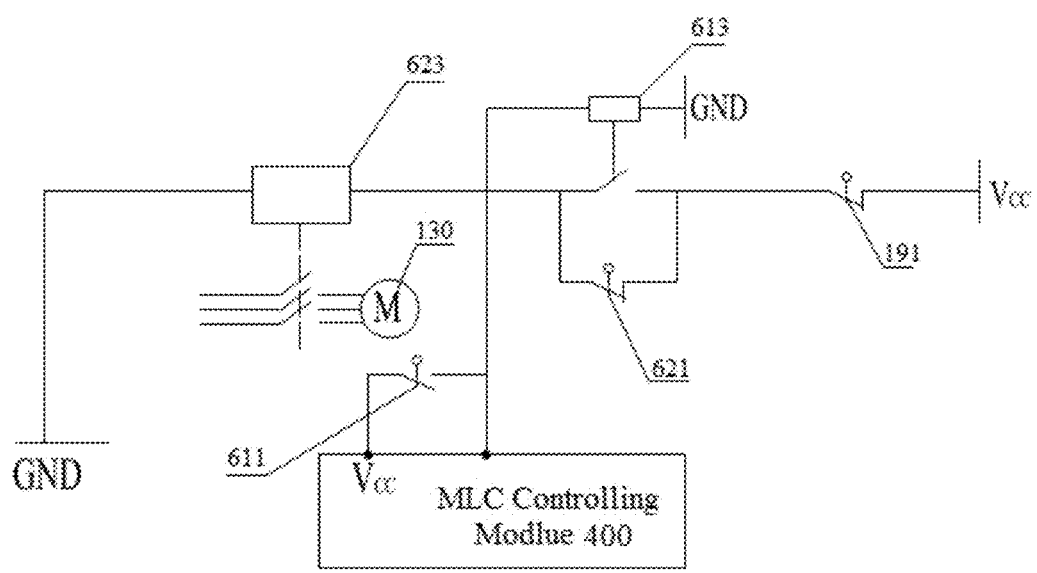
FIG. 3 is a schematic diagram illustrating an electrical structure of a device of controlling a motion position of a multi-leaf collimator according to one or more examples of the present disclosure.

Referring to FIG. 3, an end of the first back-end position detecting switch 611 is connected with a power supply $V_{CC}$ of the MLC controlling module 400, and the other end thereof is connected in series with a first relay 613. The first relay 613 is electrically connected with the MLC controlling module 400. The two ends of the second back-end position detecting switch 621 are connected in parallel with two normally open contacts of the first relay 613, and the second back-end position detecting switch 621 is connected in series with a second relay 623. The normally open contact of the second relay 623 is connected in parallel with the first motor 130.

Similarly with the first back-end position detecting switch 611 and the second back-end position detecting switch 621, the first front-end position detecting switch 612 and the second front-end position detecting switch 622 may have two relays which cooperate with each other, and may be in communication (e.g., electrically connected) with the two relays respectively in the same manner as that shown in FIG. 3.

To effectively control the trolley 110' to move within the maximum motion stroke, a limit switch 190 may be respectively provided on at least one end of the first screw rod 120', and a limit switch 190 may be in communication (e.g., electrically connected) with the MLC controlling module 400.

In an example, a back-end limit switch 191' and a front-end limit switch 192' are respectively provided at the right and left ends of the first screw rod 120', which respectively correspond to an origin position and an end position of the motion of the trolley 110'. For example, the back-end limit switch 191' and the front-end limit switch 192' may be symmetrically arranged on left and right sides of a centre position of the first screw rod 120'. In an example, the back-end limit switch 191' may be located at 40 cm to the right side of the isocenter line, and the front-end limit switch 192' may be located at 10 cm to the left side of the isocenter line.

In addition, the back-end limit switch 191' and the front-end limit switch 192' may be in communication (e.g., electrically connected) with the MLC controlling module 400, so as to respectively calibrate the origin position and the end position of the motion of the trolley 110' and to feed a calibration result back to the host computer 200 through the MLC controlling module 400.

The MLC controlling module 400 may send a stop instruction or signal to the first motor 130' when the first motor 130' drives the trolley 110' to move, and the trolley 110' moves to the right (i.e., backward) to approach the back-end limit switch 191', or moves to the left (i.e., forward) to approach the front-end limit switch 192'. However, due to inertia of the motor itself, the trolley 110' may continue to slide for a particular distance, which may cause that the overshoot of the first motor 130' occurs, the trolley 110' exceeds the maximum stroke range, or collides with the back-end limit switch 191' or the front-end limit switch 192', and the device may be even damaged.

To avoid that the overshoot of the trolley 110' occurs due to the inertia, as noted above, a first approaching switch 180' may be provided between a center of the first screw rod 120' and the front-end limit switch 192' in a way that has a preset distance with the front-end limit switch 192'. For example, the first approaching switch 180' is oriented toward the center of the first screw rod 120'. Here, the first approaching switch 180' may include a first back-end approaching switch 181' and a first front-end approaching switch 182'. The first back-end approaching switch 181' is located between the back-end limit switch 191' and the center position of the first screw rod 120'. The first front-end approaching switch 182' is located between the front-end switch 192' and the center position of the first screw rod 120'.

A distance between the back-end limit switch 191' and the first back-end approaching switch 181' is set as a deceleration buffer in which the first motor 130' moves to lift. Similarly, a distance between the front-end limit switch 192' and the first front-end approaching switch 182' is set as a deceleration buffer in which the first motor 130' moves to right. The deceleration buffer may ensure that the trolley 110' may decelerate when the trolley 110' runs to the safe distance range, for example, when approaching a boundary of a reasonable area range defined by the back-end limit switch 191' and the front-end limit switch 192', so as to prevent the overshoot. The first back-end approaching switch 181' and the first front-end approaching switch 182' may be in communication (e.g., electrically connected) with the MLC controlling module 400, respectively.

The first back-end approaching switch 181' is spaced from the back-end limit switch 191' by a preset distance. The first front-end approaching switch 182' is spaced from the front-end limit switch 192B' by the same preset distance. The preset distance may be set as 50 mm, or, the specific value of the preset distance may be set according to an actual condition.

In the example, there may be two first back-end approaching switches 181'. The two first back-end approaching switches 181' are symmetrically arranged on an upper side and a lower side of the first screw rod 120', so as to timely and accurately perceive that the trolley 110' runs into the deceleration buffer. Similarly, there may also be two first front-end approaching switches 182'. The two first front-end approaching switches 182' are symmetrically arranged on the upper side and the lower side of the first screw rod 120'.

To further prevent overshoot in a process that the first motor 130' drives the trolley 110' to move to an origin or an end, a first position detecting switch 610' and a second position detecting switch 620' may be further provided on the first screw rod 120'. The first position detecting switch 610' may include a first back-end position detecting switch 611' and a first front-end position detecting switch 612'. The second position detecting switch 620' may include a second back-end position detecting switch 621' and a second front-end position detecting switch 622'. The four position detecting switches may be in communication with (e.g., electrically connected) with the MLC controlling module 400.

The first back-end position detecting switch 611' and the second back-end position detecting switch 621' are arranged between the first back-end approaching switch 181' and the back-end limit switch 191'. The first front-end position detecting switch 612' and the second front-end position detecting switch 622' are arranged between the first front-end approaching switch 182B' and the front-end limit switch 192'.

Similarly with the first back-end position detecting switch 611 and the second back-end position detecting switch 621, the first back-end position detecting switch 611' and the second back-end position detecting switch 621' may respectively have two relays which cooperate with each other, and may be electrically connected with the two relays respectively in the same manner as that shown in FIG. 3. And the first front-end position detecting switch 612', and the second front-end position detecting switch 622' may respectively have two relays which cooperate with each other, and may be electrically connected with the two relays respectively in the same manner as that shown in FIG. 3.

In an example, as noted above, at least one guide rail 121 is further included, which is horizontally placed. The guide rail 121 may be parallel to the first screw rod 120. The trolley 110 and the trolley 110' are movably connected with the guide rail 121, so as to increase support points for the trolley 110 and the trolley 110'. Thus, the trolley 110 and the trolley 110' can be moved to left or right smoothly.

The guide rail 121 may include a guide rail 121 and a guide rail 121' arranged in parallel at the upper and lower sides of the two trolleys 110 and 110'. The upper and lower ends of the trolley 110 may be movably connected with the guide rail 121 and the guide rail 121'. Similarly, the upper and lower ends of the trolley 110' may also be movably connected with the guide rail 121' and the guide rail 121. Supported by the guide rail 121 and the guide rail 121', the trolley 110 and the trolley 110' can perform smooth translation between the guide rail 121 and the guide rail 121' when the trolley 110 or the trolley 110' is driven to move to the left or right.

According to examples of the present disclosure, a working procedure of a device of controlling a motion position of a multi-leaf collimator is described below. The device can be the device of FIGS. 1-3.

According to a mechanism and a shape of a lesion of a patient, an image is formed, and is sent to a host computer 200. The host computer 200 converts the image, determines information of a position which can be identified by an MLC controlling module 400 and is to be reached by leaves 310, and sends the information to the MLC controlling module 400. The MLC controlling module 400 issues a motion control command to a first driver 140. The first driver 140 sends a forward or backward motion instruction to a corresponding first motor 130, so that a corresponding trolley 110 carrying a plurality of pairs of the leaves 310 runs to a designated position to form a designated regular irradiation field range.

According to the specific size and shape of a lesion site of the patient, the MLC controlling module 400 sends a control instruction to a second driver 340, so that a second motor 330 is driven to move. Accordingly, a corresponding leaf 310 is driven to move to a designated position, an accurate irradiation field shape is eventually formed, e.g., a designated irregular irradiation field range, thus, preparation can be performed for accepting a X-ray dose in a next block.

Corresponding to the device of controlling a motion position of a multi-leaf collimator, the present disclosure further provides a method of controlling a motion position of a multi-leaf collimator. The method can be performed by the device of FIGS. 1-3.

Figure 4A:
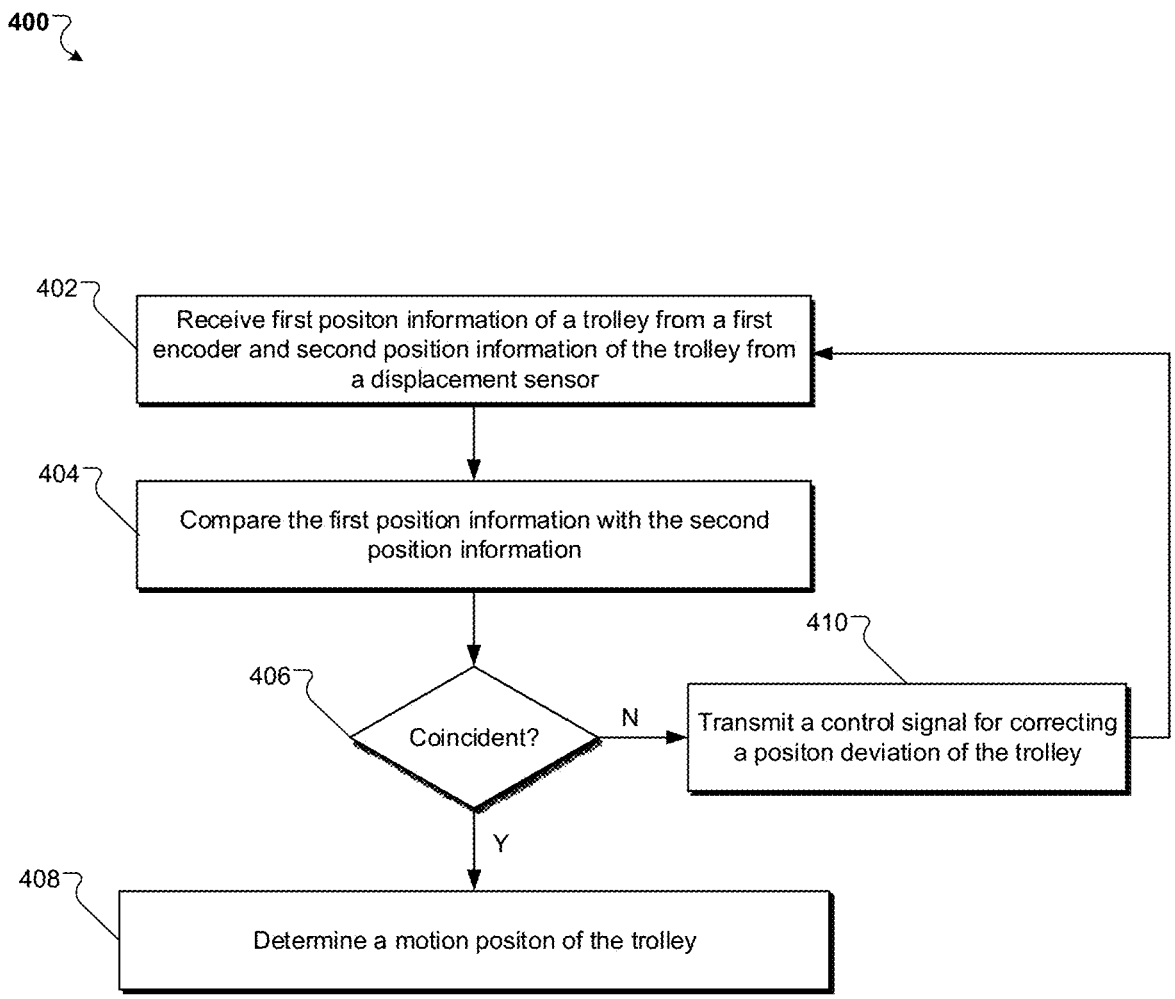
FIG. 4A is a flow chart of a process of controlling a motion position of a trolley according to one or more examples of the present disclosure.

FIG. 4A shows a flowchart of an example process 400 of performing the method. The process 400 may include procedures as follows. A first motor 130 drives a trolley 110 to move. Position information of the trolley 110 is respectively detected by a first encoder 150 and a displacement sensor 170, and is fed back to the host computer 200 through the MLC controlling module 400 (402). The host computer 200 compares first position information fed back by the first encoder 150 with second position information fed back by the displacement sensor 170 (404). The host computer 200 determines whether the first position information is coincident with (or matches with) the second position information based on a result of the comparison (406). When the first position information is coincident with the second position information, the motion position of the trolley 110 is determined, e.g., to a designation position (408). When the first position information is not coincident with the second position information, the host computer 200 sends a first motor rotation instruction to the MLC controlling module 400 to adjust a rotation angle of the first motor 130, so as to correct motion position deviation of the trolley 110 in real time (410). The process 400 then returns to step 402. In such a way, the current motion position information of the trolley 110 fed back by the first encoder 150 can be coincident with the motion position information fed back by the displacement sensor 170, the trolley 110 can be precisely controlled to move to the designated position, and accordingly the motion position of the leaves 310 arranged on the trolley 110 can be initially and precisely controlled.

Figure 4B:
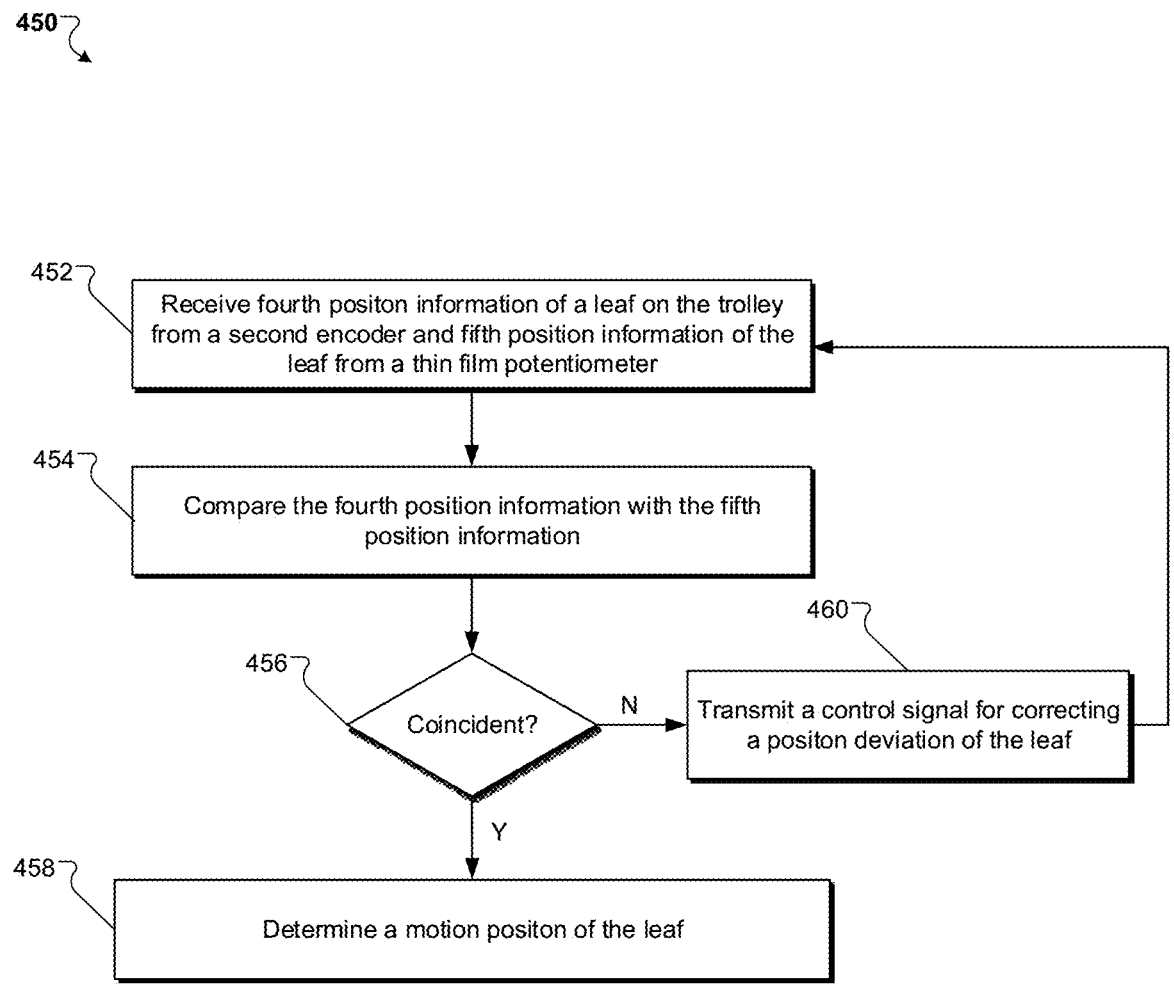
FIG. 4B is a flow chart of a process of controlling a motion position of a leaf on a trolley of a multi-leaf collimator according to one or more examples of the present disclosure.

To further precisely control motion positions of the leaves 310 to form an irradiation field similar with the shape and size of a lesion site of a patient and to improve safety performance of the device, a second motor 330 is configured to drive a corresponding leaf 310 to move to a designated position. FIG. 4B shows an example process 450 of controlling a motion position of a leaf on the trolley of FIG. 4A. The process 450 can be performed after the process 400, before the process 400, or simultaneously with the process 400. Position information of the leaf 310 is respectively detected by a second encoder 350 and a thin film potentiometer 360, and is fed back to the host computer 200 by the MLC controlling module 400 (452). The host computer 200 compares fourth position information received from the second encoder 350 with fifth position information received from the thin film potentiometer 360 (454). The host computer 200 determines whether the fourth position information is coincident with (or matches with) the fifth position information based on a result of the comparison (456). When the fourth position information is coincident with the fifth position information, the motion position of the leaf 310 is determined, e.g., to a designation position (458). When the fourth position information is not coincident with the fifth position information, the host computer 200 sends a second motor rotation instruction to the MLC controlling module 400 to adjust a rotation angle of the corresponding second motor 330, so as to correct a motion position deviation of the corresponding leaf 310 in real time (460). The process 450 then goes back to step 452. In such a way, the position information fed back by the second encoder 350 and the thin film potentiometer 360 of the same leaf 310 can be coincident with each other. Thus, the leaf 310 can be precisely controlled to move to the designated position.

In an example, two optical fiber sensors 370 respectively emit infrared ray beams. After the control system 100 including the MLC controlling module 400 and the host computer 200 is powered on, a leaf 310 moves left and right between the two infrared ray beams. When the leaf 310 moves to a position on an isocenter line 101, a photoelectric sensor 390 detects the position information of the leaf 310, and feeds the position information back to the host computer 200 through the MLC controlling module 400. After receiving the position information fed back from the photoelectric sensor 390, the host computer 200 may calculate hysteresis of a corresponding second screw rod 320 driving the leaf 310, and performs compensation for a gap of the corresponding second screw rod 320 according to the hysteresis, so that the motion position of the corresponding leaf 310 can be precisely controlled.

Further, after receiving the position information fed back by the photoelectric sensor 390, the host computer 200 may send a second motor decelerating command to the corresponding second driver 340 to drive the corresponding leaf 310 to decelerate to a specified position to prevent the overshoot of the leaf 310 due to inertia of the second motor 330 itself.

When the leaf 310 runs to a maximum stroke position, a second approaching switch 380 detects the motion position information of the leaf 310, and feeds the motion position information back to the host computer 200 through the MLC controlling module 400. After receiving the position information fed back by the second approaching switch 380, the host computer 200 may send a second motor stop instruction to the corresponding second driver 340 to drive the corresponding leaf 310 to stop the motion, so as to avoid that the leaf is damaged due to collision with an opposite leaf on the trolley 110'.

Before a leaf 310 moves, origin calibration may be performed for the leaf 310 according to a process as follows. After the second motor 330 and the leaf 310 are set at an origin position, an encoder-Z-axis detecting module 500 detects Z-axis position information of a second encoder 350. An optical fiber sensor 370 detects the position information of the corresponding leaf 310, which is taken as sixth position information. The fourth position information detected by the second encoder 350 and the sixth position information detected by the optical fiber sensor 370 are fed back to the host computer 200 through the MLC controlling module 400. The host computer 200 compares the received fourth position information with the received sixth position information, to determine whether there is any deviation. If the fourth position information is coincident with the sixth position information, it is determined that there is no deviation. If the fourth position information is not coincident with the sixth position information, the Z-axis reset calibration is performed for the corresponding second motor 350.

To precisely calibrate an origin position of a leaf 310, when the two trolleys 110, 110' and the leaves 310, 310' are at origin positions, the host computer 200 may obtain the fifth position information of the leaf 310 detected by the thin film potentiometer 360 on the leaf 310, which is taken as checking information, and may perform a comparison among the fifth position information fed back by the thin film potentiometer 360, the fourth position information fed back by the second encoder 350, and the sixth position information fed back by the optical fiber sensor 370. When the fifth position information is neither coincident with the fourth position information nor the sixth position information, it is determined that a problem exists for a position of the Z axis of the second motor 330 corresponding to the leaf 310 or for position of the optical fiber sensor 370. Therefore, re-calibration is performed for the position of the Z axis of the second motor 330 or the position of the optical fiber sensor 370, so as to ensure that repetitive deviation will not occur when the origin position is re-calibrated for the leaf 310.

When any two of the fourth position information, the fifth position information and the sixth position information are not coincident with each other, the host computer 200 may cut off a power supply of the entire control system to prevent an unpredictable condition. Meanwhile, reset calibration may be performed when the control system 100 is powered on, so as to ensure that the fourth position information fed back by the second encoder 350 is coincident with the sixth position information fed back by the optical fiber sensor 370 when the leaf 310 moves to the origin position. The origin position of each leaf 310 is accurately detected in a plurality of manners, e.g., by the second encoder 350, by the optical fiber sensor 370, and by the thin film potentiometer 360, so that the calibration may be more accurate.

When the origin calibration is performed for leaves 310, each of the leaves 310 automatically passes through a connection line of a light receiving head 372 and a light emitting head 371. When a tail end of a leaf 310 blocks the light receiving head 372, the light receiving head 372 is triggered to feed a jump signal from 1 to 0 back to the host computer 200 through the MLC controlling module 400. The light receiving head 372 further feeds an infrared ray width intercepted by the leaf 310 to the host computer 200 through the MLC controlling module 400. The host computer 200 determines whether the leaves 310 are located at the origin position according to the received feedback information from the light receiving head 372, so as to implement calibration for the origin of the leaf 310.

A working principle of performing origin calibration for the leaves 310' through an optical fiber sensor 370' is the same as that for the leaves 310 through the optical fiber sensor 370, which is not repeatedly described here.

Before a trolley 110 moves, origin calibration may be performed for the trolley according to the process as follows. After the trolley 110 is set at the origin position, the Z-axis position information of the first encoder 150 is acquired by the encoder-Z-axis detecting module 500. The position information of the trolley 110 is detected by a limit switch 190, which is taken as third position information. The first position information detected by the first encoder 150 and the third position information detected by the limit switch 190 are fed back to the host computer 200 by the MLC controlling module 400. The host computer 200 compares the first position information with the third position information. When the first position information is not coincident with the third position information, reset calibration is performed for the Z axis of the first motor 130. Specifically, the trolley 110 is driven by the first motor 130 to move slowly to the left or to the right to reach into a designated range of the limit switch 190, so as to ensure that the trolley 110 is at the origin position.

To accurately calibrate the origin position of the trolley 110, when the trolley 110 is at the origin position, the host computer 200 may acquire second position information detected by a displacement sensor 170, and may compare the second position information detected by the displacement sensor 170 taken as checking information respectively with the first position information fed back by the first encoder 150 and the third position information fed back by the limit switch 190. When the second position information is neither coincident with the first position information nor the third position information, it is determined that a problem exists for the position of the Z axis of the first motor 130 or the position of the limit switch 190. The two positions may be re-calibrated, so as to ensure that there is no repetitive deviation when the origin position calibration is performed for the trolley 110 again.

When any two of the second position information detected by the displacement sensor 170, the first position information fed back by the first encoder 150 and the third position information fed back by the back-end limit switch 191 are not coincident with each other, the host computer 200 may cut off a power supply of the entire control system to prevent an unpredictable condition. Reset calibration may be performed when the control system 100 is powered on, so as to ensure that the first position information fed back by the first encoder 150 and the third position information fed back by the limit switch are coincident when the trolley 110 moves to the origin position or end position. The origin position calibration is performed for the trolley 110 in a plurality of manners, e.g., by the first encoder 150, by the limit switch 190 and by the displacement sensor 170, so as to perform accurate calibration.

When the trolley 110 moves to the position of the limit switch 190, the limit switch 190 sends a jump signal from 1 to 0 to the host computer 200 through the MLC controlling module 400, which indicates that the trolley 110 is at the origin position or the end position, and the calibration information of the origin position or the end position of the trolley is further provided.

When the trolley 110 moves to the position of the limit switch 190, to avoid that the first motor 130 drives the trolley 110 to move beyond a safe distance range and an unexpected condition occurs due to the inertia of the first motor 130 itself, the following control may be performed. The position information of the trolley 110 is fed back to the MLC controlling module 400 by a first approaching switch 180. And the position information received from the first approaching switch 180 is sent to the host computer 200 by the MLC controlling module 400. After receiving the position information fed back from the first approaching switch 180, the host computer 200 sends a first motor deceleration command to a first driver 140 through the MLC controlling module 400 to drive the trolley 110 to decelerate to the position of the limit switch 190. Further, after the trolley 110 touches the button of the limit switch 190, the limit switch 190 generates a trolley motion stop signal, and feeds the stop signal back to the host computer 200, which indicates that the corresponding trolley 110 reaches the origin or end position, so as to ensure that the position of the trolley 110 is accurate.

When the trolley 110 moves to the limit switch 190, a first position detecting switch 610 and a second position detecting switch 620 provided between the limit switch 190 and the first approaching switch 180 may be used to further avoid that the first motor 130 drives the corresponding trolley 110 to move beyond a safe distance range due to the inertia of the first motor 130 itself, and an unexpected condition occurs.

Here, to describe a working principle of a position detecting switch, it is taken as an example that the trolley 110 moves left to a back-end limit switch 191. A first back-end position detecting switch 611 is set as a normally open contact. A second back-end position detecting switch 621 is set as a normally closed contact.

When the trolley 110 runs left to a first back-end approaching switch 181, a first motor 130 enters a deceleration area. When the trolley 110 passes through the first back-end position detecting switch 611, a contact point of a first relay 613 is closed. The information that the contact point of the first relay 613 is closed is fed back to the host computer 200 through the MLC controlling module 400. In this way, a coil of the first relay 613 is powered on, and is attracted to shield the second back-end position detecting switch 621. A coil of a second relay 623 is energized to ensure that the first motor 130 can be powered on by a power supply in a way that the trolley 110 is capable of stopping when moving to a corresponding position. The host computer 200 may further send a deceleration instruction for the first motor 130 to a first driver 140 through the MLC controlling module 400 according to the position information of the trolley 110 fed back by the first back-end position detecting switch 611 and the second back-end position detecting switch 621, so that the first motor 130 can be driven to decelerate and the trolley 110 slowly runs left to the back-end limit switch 191.

When the trolley 110 runs left to the first back-end approaching switch 181, the first motor 130 enters a deceleration area. If the first back-end position detecting switch 611 fails when the trolley 110 passes through the first back-end position detecting switch 611, the coil of the first relay 613 is further in a de-energized state, and a contact point of the first relay 613 is in an normally open state. When the trolley 110 runs to the second back-end position detecting switch 621, since a pair of contact points of the first relay 613 are in a normally open state, the coil of the first relay 613 is de-energized, and the coil of the second relay 623 for controlling the trolley 110 is also de-energized, and a circuit between the first motor 130 and the power supply of the first motor 130 is cut off in a way that the trolley is capable of stopping at the limit switch. In this way, the first back-end position detecting switch 611, the second back-end position detecting switch 621, the first relay 613 and the second relay 623 cooperate with each other to cut off the power supply of the first motor 130 on electrical hardware, in a way that the trolley 110 can be immediately stopped when it is detected that the first back-end position detecting switch 611 fails, thereby preventing overshoot.

The working principle that the overshoot of the first motor 130 is avoided through a first front-end position detecting switch 612 and a second front-end position detecting switch 622 is the same as the working principle that the overshoot of the first motor 130 is avoided through the first back-end position detecting switch 611 and the second back-end position detecting switch 621, which is not repeatedly described here. The principle of electrically avoiding the overshoot of the first motor 130' by performing cooperation among a first position detecting switch 610', a second position detecting switch 620' and the relay is also similar to that above.

It should be noted that methods and devices of controlling a motion position of a multi-leaf collimator described above may further be applied to a medical linear accelerator.

In examples of the present disclosure, motion positions of a trolley and a leaf can be accurately controlled by performing multiplex motion position detections, multiplex origin position checks and multiplex design of avoiding overshoot for the trolley and the leaf in the MLC, so that an irradiation field with a suitable shape and size is effectively formed, a healthy site of a patient can be avoided to be suffered from unnecessary X-ray irradiation, safety of patients and medical workers can be protected, and reliability of the system can be improved.

The methods, processes and units described herein may be implemented by hardware (including hardware logic circuitry), software or firmware or a combination thereof. The term 'processor' is to be interpreted broadly to include a processing unit, ASIC, logic unit, or programmable gate array etc. The processes, methods and functional units may all be performed by the one or more processors; reference in this disclosure or the claims to a 'processor' should thus be interpreted to mean 'one or more processors'.

The figures are only illustrations of an example, wherein the units or procedure shown in the figures are not necessarily essential for implementing the present disclosure. Those skilled in the art will understand that the units in the device in the example may be arranged in the device in the examples as described, or may be alternatively located in one or more devices different from that in the examples. The units in the examples described may be combined into one module or further divided into a plurality of sub-units.

Although the flowcharts described show a specific order of execution, the order of execution may differ from that which is depicted. For example, the order of execution of two or more blocks may be changed relative to the order shown. Also, two or more blocks shown in succession may be executed concurrently or with partial concurrence. All such variations are within the scope of the present disclosure.

For simplicity and illustrative purposes, the present disclosure is described by referring mainly to an example thereof. In the above description, numerous specific details are set forth to provide a thorough understanding of the present disclosure. It will be readily apparent however, that the present disclosure may be practiced without limitation to these specific details. In other instances, some methods and structures have not been described in detail so as not to unnecessarily obscure the present disclosure.

In the description of the present disclosure, it is to be understood that the orientation or positional relationship indicated by the terms such as "upper", "lower", "left", "right" and the like is based on the orientation or the positional relationship shown in the drawings, which are merely for ease of description of the present disclosure and the simplification of description, rather than indicating or implying that the device or elements referred to must have a particular orientation and are constructed and operated in a particular orientation and are therefore not to be construed as limiting the present disclosure.

The terms such as "first" and "second" are for the purpose of description merely and are not to be construed as indicating or implying relative importance or implicitly indicating the number of technical features indicated. Thus, the feature that is defined by "first" and "second" may expressly or implicitly include one or more of the features. In the description of the present disclosure, the meaning of "a plurality of" refers to two or more, unless otherwise specified.

As used herein, the terms "a" and "an" are intended to denote at least one of a particular element, the term "includes" means includes but not limited to, the term "including" means including but not limited to, and the term "based on" means based at least in part on. Throughout the present disclosure, the word "include", or variations such as "includes" or "including", will be understood to imply the inclusion of a stated element, integer or block, or group of elements, integers or blocks, but not the exclusion of any other element, integer or block, or group of elements, integers or blocks.

It will be appreciated by persons skilled in the art that numerous variations and/or modifications may be made to the above examples, without departing from the broad general scope of the present disclosure. The present examples are, therefore, to be considered in all respects as illustrative and not restrictive.

The invention claimed is:

1. A device for controlling a motion position of a multi-leaf collimator, the multi-leaf collimator having two rows of leaves arranged in opposite sides, wherein the device comprises:
a control system;
two trolleys connected with the control system, wherein each of the trolleys carries a respective row of the leaves and is movably connected with a first screw rod and driven by a first motor connected with the first screw rod;
a first encoder arranged on the first motor and operable to feed back first position information of the trolley to the control system;
a displacement sensor arranged on the first screw rod and operable to feed back second position information of the trolley to the control system, wherein the control system is operable to control the motion position of the trolley based on the first position information and the second position information;
a limit switch arranged on at least one end of the first screw rod, wherein the limit switch is in communication with the control system; and
a first approaching switch arranged between a center of the first screw rod and the limit switch in a way that the first approaching switch has a preset distance with the limit switch, wherein the first approaching switch is in communication with the control system.

2. The device according to claim 1, further comprising:
a first position detecting switch and a second position detecting switch arranged between the limit switch and the first approaching switch on the first screw rod, wherein the first position detecting switch and the second position detecting switch are in communication with the control system,
wherein the first position detecting switch is connected in series with a first relay in communication with the control system,
wherein the second position detecting switch is connected in series with a second relay connected in parallel with the first relay, and
wherein the second relay is connected in parallel with the first motor to electrically control a power supply of the first motor.

3. The device according to claim 2, wherein:
the first position detecting switch is set as a normally open contact,
the second position detecting switch is set as a normally closed contact,
the second position detecting switch is connected in parallel with a normally open contact of the first relay, and
the first motor is connected in parallel to a normally open contact of the second relay.

4. The device according to claim 1, wherein each row of the leaves comprises a plurality of leaves, and each of the leaves is driven by a respective second screw rod and a respective second motor,
wherein a second encoder is arranged on the second motor and operable to feed back fourth position information of the leaf to the control system,
wherein a thin film potentiometer is arranged on the leaf and operable to feed back fifth position information of the leaf to the control system, and
wherein the control system is operable to control a motion position of the leaf based on the fourth position information and the fifth position information.

5. The device according to claim 1, further comprising:
an optical fiber sensor arranged on an end side of each row of the leaves.

6. The device according to claim 5, wherein the optical fiber sensor comprises:

a light emitting head; and
a light receiving head,
wherein the light emitting head and the light receiving head are respectively arranged at two opposite ends of the end side, and
wherein the light receiving head is in communication with the control system.

7. The device according to claim 1, further comprising:
a photoelectric sensor arranged on a center line between the two rows of leaves and on an outside of the two rows of leaves,
wherein the photoelectric sensor is in communication with the control system.

8. The device according to claim 1, further comprising:
a second approaching switch arranged on two sides of a center line between the two rows of leaves and on an outside of the two rows of leaves,
wherein the second approaching switch is in communication with the control system.

9. The device according to claim 1, further comprising:
at least one guide rail parallel to the first screw rod,
wherein each of the trolleys is movably connected with the at least one guide rail.

10. A method of controlling a motion position of a multi-leaf collimator, comprising:
transmitting a control signal to a first motor to drive a trolley to move, the trolley being movably connected to a first screw rod and carrying a row of leaves arranged on a side of the multi-leaf collimator;
receiving first position information of the trolley from a first encoder arranged on the first motor;
receiving second position information of the trolley from a displacement sensor arranged on the first screw rod;
receiving third position information of the trolley from a limit switch when the trolley is at an origin position, wherein the limit switch is located on an end of the first screw rod;
receiving motion position information of the trolley detected by a first approaching switch when the trolley moves along the first screw rod to the first approaching switch, wherein the first approaching switch is located between the limit switch and a center of the first screw rod and has a preset distance with the limit switch;
comparing the first position information with the second position information to determine whether the first position information is coincident with the second position information; and
when the first position information is determined not to be coincident with the second position information, adjusting a rotation angle of the first motor to correct a deviation of the motion position of the trolley.

11. The method according to claim 10, further comprising:
comparing the third position information with the first position information and the second position information, respectively;
when the first position information is determined not to be coincident with the third position information based on a result of the comparison, performing a reset calibration for Z axis of the first motor;
when the second position information is determined to be neither coincident with the first position information nor the third position information based on the result of the comparison, calibrating at least one of the Z axis of the first motor or a position of the limit switch; and
when any two of the first position information, the second position information, and the third position information are determined not to be coincident with each other based on the result of the comparison, cutting off a power supply to the multi-leaf collimator.

12. The method according to claim 11, further comprising:
controlling the first motor to decelerate rotation based on the received motion position information in a way that the trolley is capable of stopping at the limit switch.

13. The method according to claim 10, further comprising:
transmitting a second control signal to a second motor to drive one of leaves to move, wherein each of the leaves is movably connected to a respective second screw rod and driven by a respective second motor;
receiving fourth position information of the leaf from a second encoder arranged on the second motor;
receiving fifth position information of the leaf from a thin film potentiometer arranged on the leaf;
comparing the fourth position information with the fifth position information to determine whether the fourth position information is coincident with the fifth position information; and
when the fourth position information is determined not to be coincident with the fifth position information, adjusting a rotation angle of the second motor to correct a position deviation of the leaf.

14. The method according to claim 13, further comprising:
receiving sixth position information of the leaf from an optical fiber sensor when the leaf is at an origin position, wherein the optical fiber sensor is located on an end side of the row of leaves to which the leaf belongs;
comparing the sixth position information with the fourth position information and the fifth position information, respectively;
when the sixth position information is determined not to be coincident with the fourth position information based on a result of the comparison, performing a reset calibration for Z axis of the second motor;
when the fifth position information is determined to be neither coincident with the fourth position information nor the sixth position information based on the result of the comparison, calibrating at least one of the Z axis of the second motor or the position of the optical fiber sensor; and
when any two of the fourth position information, the fifth position information, and the sixth position information are determined not to be coincident with each other based on the result of the comparison, cutting off a power supply to the multi-leaf collimator.

15. The method according to claim 13, further comprising:
receiving a position information of the leaf from a photoelectric sensor, wherein the row of leaves is opposite to a second row of leaves carried by a second trolley and arranged on a second, opposite side of the multi-leaf collimator, and wherein the photoelectric sensor is arranged on a center line between the two rows of leaves and on an outside of the two rows of leaves; and
performing a hysteresis compensation for the second screw rod according to the position information received from the photoelectric sensor.

16. The method according to claim 13, further comprising:
receiving a position information of the leaf from a second approaching switch when the leaf moves along the second screw rod to a maximum stroke position, wherein the row of leaves is opposite to a second row of leaves carried by a second trolley and arranged on a second, opposite side of the multi-leaf collimator, and wherein the second approaching switch is arranged at one of two sides of a center line between the two rows of the leaves and on an outside of the two rows of leaves; and controlling the second motor to stop rotating according to the position information received from the second approaching switch.

17. A linear accelerator comprising:
a multi-leaf collimator having two rows of leaves arranged on opposite sides; and
a motion position controlling device comprising:
    a control system;
    two trolleys connected with the control system, wherein each of the trolleys carries a respective row of the leaves and is movably connected with a first screw rod and driven by a first motor connected with the first screw rod;
    a first encoder arranged on the first motor and operable to feed back first position information of the trolley to the control system;
    a displacement sensor arranged on the first screw rod and operable to feed back second position information of the trolley to the control system, wherein the control system is operable to control the motion position of the trolley based on the first position information and the second position information;
    a limit switch arranged on at least one end of the first screw rod, wherein the limit switch is in communication with the control system; and
    a first approaching switch arranged between a center of the first screw rod and the limit switch in a way that the first approaching switch has a preset distance with the limit switch, wherein the first approaching switch is in communication with the control system.

18. The linear accelerator according to claim 17, wherein each row of the leaves comprises a plurality of leaves, and each of the leaves is driven by a respective second screw rod and a respective second motor,
    wherein a second encoder is arranged on the second motor and operable to feed back fourth position information of the leaf to the control system,
    wherein a thin film potentiometer is arranged on the leaf and operable to feed back fifth position information of the leaf to the control system, and
    wherein the control system is operable to control a motion position of the leaf based on the fourth position information and the fifth position information.

* * * * *